US007597691B2

(12) United States Patent
Kawaguchi et al.

(10) Patent No.: US 7,597,691 B2
(45) Date of Patent: Oct. 6, 2009

(54) LIQUID STORAGE BAG

(75) Inventors: Yumi Kawaguchi, Kanagawa (JP); Toru Ikeda, Kanagawa (JP); Yoshihiro Kobayashi, Kanagawa (JP); Shozo Taguchi, Tokyo (JP); Yoshikatsu Tomita, Osaka (JP)

(73) Assignees: Ajinomoto Co., Inc., Tokyo (JP); Nipro Corporation, Osaka-shi (JP)

( * ) Notice: Subject to any disclaimer, the term of this patent is extended or adjusted under 35 U.S.C. 154(b) by 359 days.

(21) Appl. No.: 10/257,956

(22) PCT Filed: Apr. 23, 2001

(86) PCT No.: PCT/JP01/03454

§ 371 (c)(1),
(2), (4) Date: Oct. 24, 2002

(87) PCT Pub. No.: WO01/80806

PCT Pub. Date: Nov. 1, 2001

(65) Prior Publication Data

US 2003/0148004 A1 Aug. 7, 2003

(30) Foreign Application Priority Data

Apr. 24, 2000 (JP) ............................ 2000-121955

(51) Int. Cl.
*A61B 19/00* (2006.01)

(52) U.S. Cl. ...................... 604/408; 604/410; 604/403; 383/210.1

(58) Field of Classification Search ......... 604/408–410, 604/905; 220/62.22; 206/363–366; 383/210.1, 383/210, 67
See application file for complete search history.

(56) References Cited

U.S. PATENT DOCUMENTS

| | | | | | |
|---|---|---|---|---|---|
| 4,610,684 | A | * | 9/1986 | Knox et al. | 604/416 |
| 4,637,061 | A | * | 1/1987 | Riese | 383/38 |
| 4,869,725 | A | * | 9/1989 | Schneider et al. | 604/408 |
| 5,195,658 | A | * | 3/1993 | Hoshino | 222/92 |
| 5,209,347 | A | * | 5/1993 | Fabisiewicz et al. | 206/219 |
| 5,525,363 | A | * | 6/1996 | Herber et al. | 426/130 |
| 5,928,213 | A | * | 7/1999 | Barney et al. | 604/410 |
| 6,743,451 | B2 | * | 6/2004 | Rasile et al. | 426/112 |

FOREIGN PATENT DOCUMENTS

| | | |
|---|---|---|
| JP | 57-86275 | 5/1982 |
| JP | 64-6248 | 1/1989 |
| JP | 7-209976 | 8/1995 |
| JP | 11-285518 | 10/1999 |

* cited by examiner

*Primary Examiner*—Leslie R Deak
(74) *Attorney, Agent, or Firm*—Oblon, Spivak, McClelland, Maier & Neustadt, L. L. P.

(57) ABSTRACT

A liquid storage bag having a partition wall allowed to be peeled easily and not peeled by an accidental drop, etc. The liquid storage bag is one wherein the upper part thereof is closed with a freely and closable zipper, the bottom thereof is provided with a liquid outlet, and an easily peelable partition wall (a weak seal part) is provided close to the zipper. The internal space of the liquid storage bag is divided liquid-tightly into upper and lower parts through this weak seal part, liquid is stored in the lower part of the internal space (liquid storage chamber), and the weak seal part is formed in outside-convex form at a center and increased in width at both end parts thereof.

9 Claims, 2 Drawing Sheets

LIQUID STORAGE BAG

TECHNICAL FIELD

The present invention relates to a liquid storage bag containing liquid preliminarily. More particularly, it relates to an improvement in the liquid storage bag which is the subject matter of the invention involving in Japanese Patent Application Laid-Open No. Hei 11-285518.

BACKGROUND ART

A process has been heretofore applied to a patient who is difficult to take nutrients from the mouth in which an enteral nutrient is infused to the patient through a catheter inserted from the mouth and the nose. Specifically, the enteral nutrient stored in its bag or bottle is infused in the body of the patient through an infusion set or a catheter. The enteral nutrient is prepared by adding water or warm water to a concentrated liquid or powdery enteral nutrient. After prepared in another vessel the prepared enteral nutrient is poured from the vessel into a bag or bottle for enteral nutrient. Alternatively, the enteral nutrient is directly prepared in a bag or bottle for enteral nutrient. However, the method wherein the prepared enteral nutrient is poured into the bag or bottle after prepared in another vessel involves a trouble that the use of another clean vessel is needed and further has the disadvantage that there is a high risk of mixing a dust or the like therein. A method of preparing the enteral nutrient directly in a bag is disclosed in, for example Japanese Patent Application Laid-Open No. Sho 57-86275. The bag disclosed therein is a bag container stored a solid or liquid substance which is dispersible or dissoluble in a liquid, said bag container having a resealable liquid inlet. There are disclosed in the example thereof a liquid inlet composed of a zipper, the outer part of the zipper being further provided with a heat seal part and the heat seal part to be cut off by scissors for use, etc. However, the bag container having the liquid inlet composed of a zipper alone has the disadvantages in that it has a poor sealing property so that it adversely affects on the quality of the enteral nutrient stored therein, and it is difficult in the virgin proof (tamper proof). Also, the bag container wherein the outer part of the zipper is provided with the heat seal part has a defect that the operation efficiency is bad because scissors must be used.

So, one of the present applicants proposed already a liquid storage bag as shown in Japanese Patent Application Laid-Open No. Hei 11-285518 as one of solving the disadvantages as stated above. In the bag, as shown in FIG. 2, the upper part thereof is closed with a freely openable and closable closing means, the bottom thereof is provided with a liquid exit, the internal space thereof is divided liquid-tightly into upper and lower parts through an easily peelable partition wall which is provided close to the closing means, and liquid is stored in the divided lower internal space. However, this bag has the disadvantage that when the width of the partition wall is made small, the partition wall may peel off by an accidental drop thereof, etc. while when the width of the partition plate is made large, it is hard to peel off, and hence some improvements were still needed for the bag.

DISCLOSURE OF THE INVENTION

The present invention has been made in the light of the above circumstances, and its object is to provide a liquid storage bag provided with a partition wall which may be easily peeled off and which does not peel off by an accidental drop thereof, etc.

As a result of having ardently studied to solve the above object, the present inventors have completed the present invention based on their concept that by increasing the width of the partition wall at the both end parts thereof, the peeling of the partition wall by an accidental drop might be prevented and by forming the center part of the partition wall into outside-convex form the peeling thereof would become easy. That is, the present invention relates to an improved liquid storage bag wherein the upper part of the bag body is closed with a freely openable and closable closing means, a liquid exit is provided at the bottom, the internal space of the bag body is divided liquid-tightly into upper and lower parts through an easily peelable partition wall provided close to the closing means and liquid is stored in the divided lower part. The partition wall is formed in outside-convex form at a center and increased in width at both end parts thereof.

In the present invention, in order to prevent the upper part in the internal wall of the bag from being contaminated, the part upper than the closing means may be sealed to enclose the closing means. A notch for making the seal part removable easily may be formed at the side seal part enclosing the closing means. Also, it is preferable that the width in the both end parts of the partition wall is two times or more that in the center part. Also, as the closing means a zipper is preferable. It is preferable that the upper part adjacent to the both end parts of the zipper is heat-sealed so that leakage of liquid never occurs after a liquid preparation has been prepared in the bag and the zipper has been closed. As a liquid to be stored in the internal part, a concentrated enteral nutrient is preferable.

BRIEF EXPLANATION OF DRAWINGS

In FIG. 1, 1 indicates a liquid storage chamber, 2 does a zipper (a closing means), 3 does a weak seal part (an easily peelable partition wall), 31 does a central part, 32 does both end parts, 4 does a liquid exit, 5 does a hanging hole, 6 does a feeding open, 7 does the heat seal part, 8 does the seal part and 9 does a notch.

In FIG. 2, 1 indicates the bag body, 11 does a hanging hole, 2 does a liquid exit, 21 does a closing member, 3 does a zipper, 4 does a partition wall, 41 does a weak seal part and 5 does a feeding open.

THE BEST MODE FOR CARRYING OUT THE INVENTION

Figure 1:
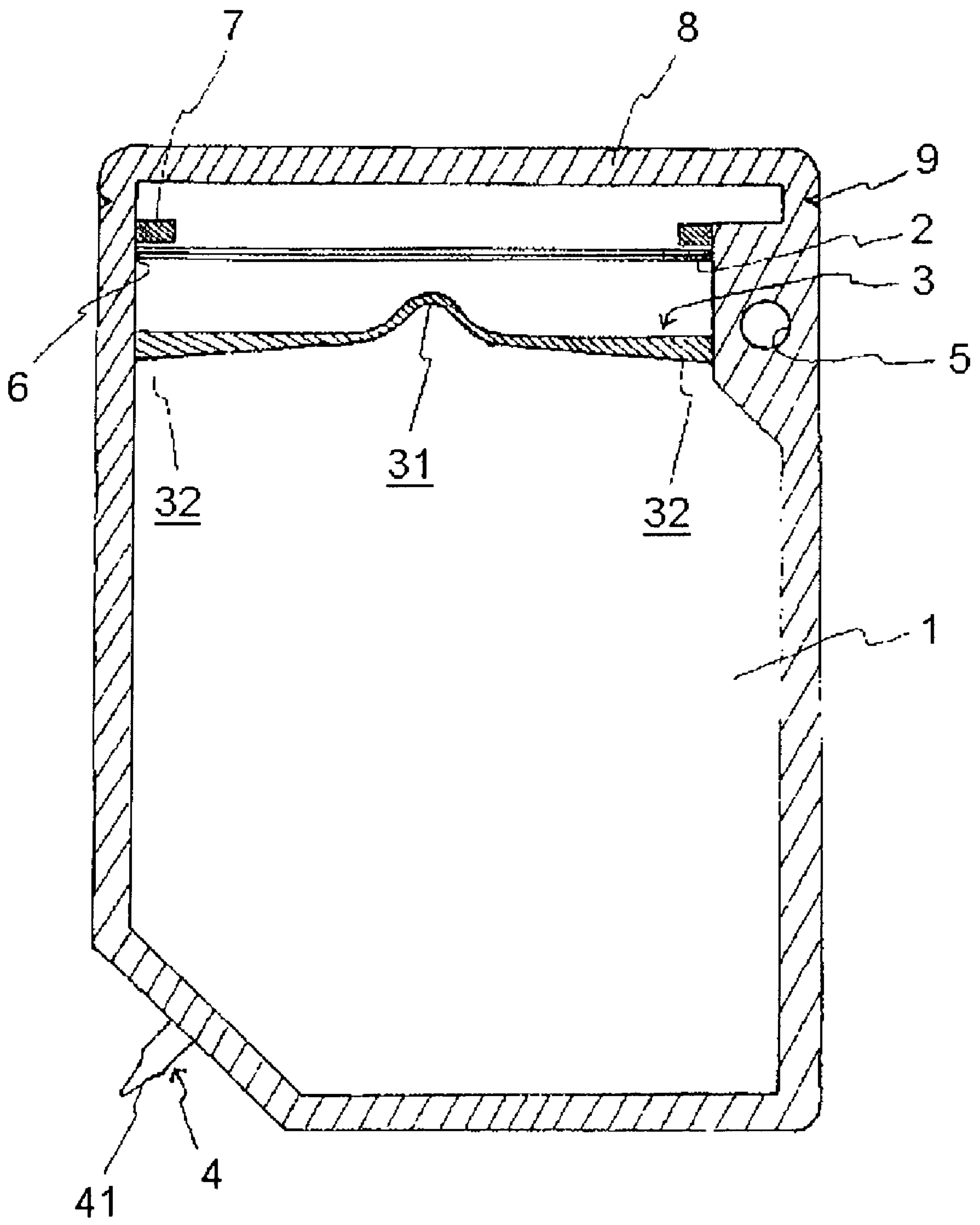
FIG. 1 is a schematic plain view indicating an example of the present invention.
Figure 2:
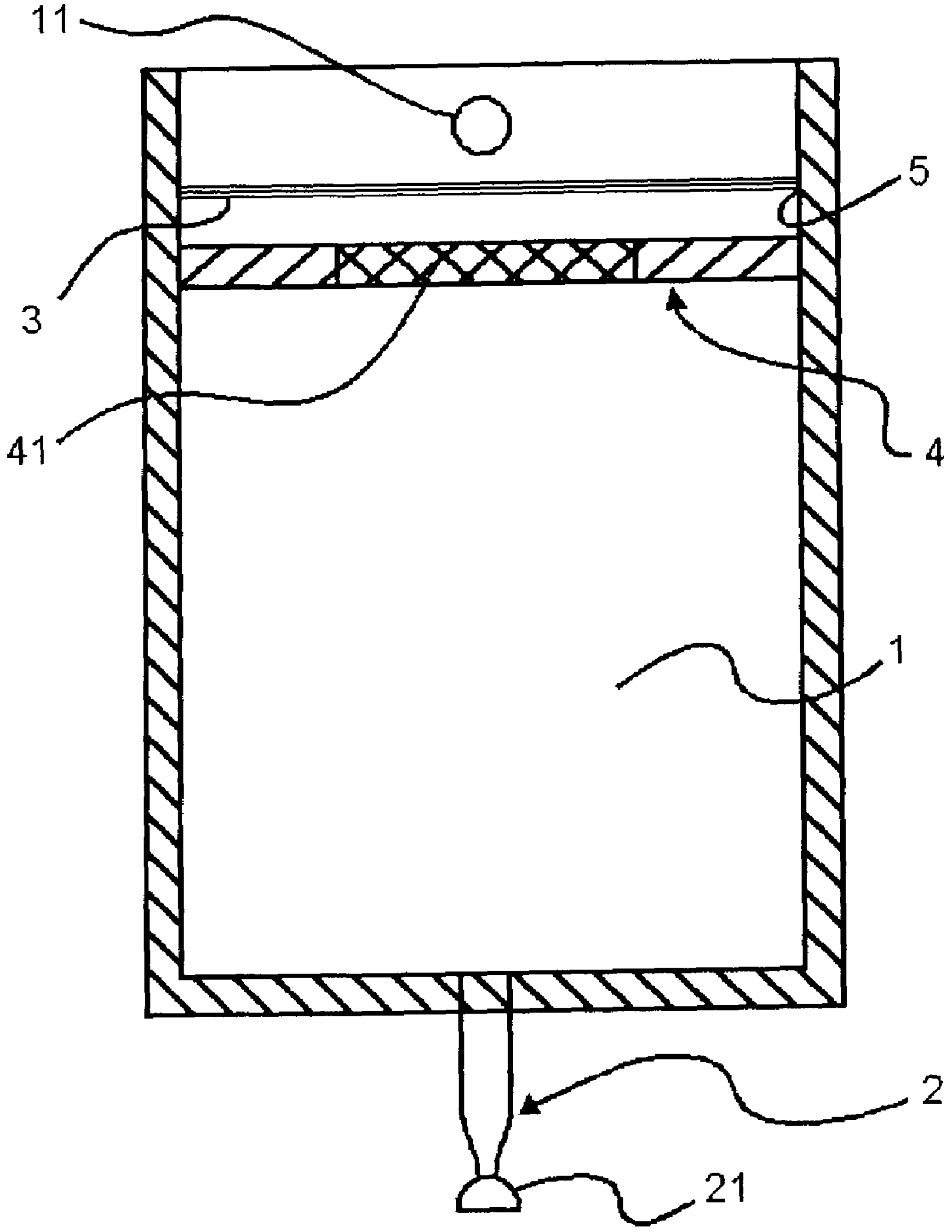
FIG. 2 is a plain view of a liquid storage bag disclosed in Japanese Patent Application Laid-Open No. Hei 11-285518.

Next, an example of the present invention is illustrated based on the drawing.

In the liquid storage bag shown in FIG. 1, the upper part is closed with a freely openable and closable zipper 2, a liquid exit 4 is provided at the bottom, and an easily peelable partition wall (a weak seal part 3) is provided close to the zipper 2. The internal space of the liquid storage bag is divided liquid-tightly into upper and lower parts through this weak seal part 3 and liquid is stored in the lower internal space (liquid storage chamber 1). And, the weak seal part 3 is formed in outside-convex form at a center part 31 and increased in width at both end parts 32 thereof.

The liquid storage bag is one wherein two superposed sheets of a synthetic resin sheet (includes laminated sheet) such as polyethylene, polypropylene, polyamide (PA), polyester (PET), ethylene-vinyl acetate copolymer or the like is heat sealed together at the periphery to form a bag, and the upper part of the bag is provided with the closing means (the zipper 2) and with the weak seal part 3 close to the zipper 2, and the bottom is provided with the liquid exit 4. And liquid is stored in the internal space below the weak seal part 3 (liquid storage chamber 1).

In case that liquid to be stored in the liquid storage chamber 1 is one which should be preserved for a long period of time or which is susceptible to oxidation, the oxygen impermeable synthetic resin sheet such as aluminum foil laminated one may be preferably used. For preventing oxidation of liquid, at least the liquid storage chamber 1 may be coated with an aluminum foil or the like. If necessary, a hanging hole 5 is provided at the upper part of the liquid storage bag, and thereby the bag can be hanged from a drop stand for use. A hanging means does not limited to the hanging hole 5 and it may also be e.g., a loop-like string secured to the upper part of the bag.

The upper part of the liquid storage chamber constitutes the feeding open 6 for feeding water or warm water which dilutes the preliminarily stored liquid, e.g., a concentrated enteral nutrient and the feeding open 6 is closed with a zipper 2 serving as a freely openable and closable closing means. This zipper 2 has a structure to be closed by fitting a convex stripe into a concave stripe and can be opened and ( closed when so required, said convex and concave stripes being respectively formed to the inner wall of the bag located in opposed positions. Incidentally, in case that the feeding open 6 is molded in cylindrical shape, the cover body to be fitted into said feeding open 6 may also be used as the closing means. Here, in order to prevent the contamination of the inner wall located at the upper part of the bag, the part upper than the zipper 2 may be sealed to enclose it. The side part of the seal part 8 enclosing the zipper 2 may be formed with a notch 9 for making the seal part removable. Also, it is preferable that the upper parts adjacent to the both end parts of the zipper 2 are provided with the heat seal 7 by a method such as heat seal so that leakage of the liquid never occurs after the liquid preparation has been prepared in the bag and the zipper 2 has been closed.

The internal space of the bag is divided liquid-tightly into upper and lower parts through an easily peelable partition wall such as the weak seal part 3 provided at a lower part than the zipper 2 and close thereto. This weak seal part 3 is one which can be easily peeled off and opened by pressing the liquid storage chamber 1 from the outside. For example, the weak seal part 3 can be formed by inserting a weak seal sheet between the sheets forming the bag and heat sealing these sheets together. It can also be formed by pressing into a belt shape the sheets forming the bag from the outside while the temperature is controlled so as not to seal the sheets together. The weak seal part 3 is formed in a shape projected upward the so-called outside-convex form at a center part 31 and increased gradually in width toward both end parts 32 thereof. By forming the center part into a convex shape, namely outside-convex form, the peeling occurred at a part of the center part 31 is spread along the line of outside-convex form for opening. Also, by forming the width of the seal so as to become increasing gradually toward both end parts 32, the peeling of the weak seal part 3 can be prevented which tends to occur at the both end parts thereof by impact from the dropping. The width of the end parts 32 of the weak seal part 3 is 2 times or more, preferably 3 times or more as broad as that of the center part 31. Incidentally, although the weak seal part 3 is provided close to the zipper 2, when provided at too close position, during opening the weak seal part 3 there is a fear that the zipper 2 may also be opened unintentionally, and hence it is preferable to leave the distance of 5 mm or more between them.

EXPERIMENTAL EXAMPLE

The liquid storage bag of the present invention whose feature lies in the weak seal part (Example) and the liquid storage bag before improvement (Comparative Example) each made of a plastic laminate sheet having 99 μm in thickness was subjected to the opening test of the weak seal part by the dropping (a drop test). There were obtained the results as shown in table 1. Incidentally, the size of the liquid storage bags was 280 mm in height and 200 mm in side. The width of the heat seal in the seal part was 10 mm and its seal strength was 40 N/15 mm, and the heat seal strength of the weak seal part was 12 N/15 mm. Also, the width of the weak seal part was 3 mm at the center part and 8 mm at each of both end parts in Example while in Comparative Example it was equally 3 mm. Also, the drop test was conducted in a case unit (containing 18 bags). The test was performed on each of 2 cases in Example while it was done on each of 3 cases in Comparative Example.

A drop method was applied wherein the case was placed for 24 hours for humidity-control under an atmosphere of 20 ° C. and 65% RH and thereafter dropped 6 times from the height of 60 cm (when dropped, the place to collide on the floor: 1 time at the corner, 3 times at the edge and 2 times at the side) and dropped 2 times from the height of 90 cm (when dropped, the place to collide on the floor: the bottom).

Also, as the laminated sheet made of plastic material, there was used a laminated sheet comprising an outer layer of polyester (polyethylene terephthalate:PET) and an inner layer of undrawn polypropylene: PET/metallized PET/PA/CPP wherein a trade name "PC", a product of Unitika Ltd. was used as PET; a trade name "1031HG", a product of Toyo Metallizing Co., Ltd. as metallized PET; a trade name "ONM-BRT", Unitika Ltd. as PA, a trade name "C1506", Toyobo Co., Ltd. as CPP and polypropylene (a trade name "9501-improved", a product of Toray Plastic Films Co., Ltd.) as a weak seal sheet.

It can be seen from table 1 that in the case of the liquid storage bag of the present invention, the opening of the weak seal part in the liquid storage bag by an accidental drop can be prevented.

TABLE 1

| | Number of Broken Bag | Peeling of The Weak Seal Part |
|---|---|---|
| Example 1 | 0 | 0 |
| Example 2 | 0 | 0 |
| Comparative Example 1 | 0 | 2 |
| Comparative Example 2 | 0 | 4 |
| Comparative Example 3 | 0 | 4 |

In using the liquid storage bag of the present invention, first the seal part 8 enclosing the zipper 2 is removed by tearing the bag from the notch 9 and subsequently the liquid storage chamber 1 is pressed from the outside so as to peel off and open the weak seal part 3, and thereafter the zipper 2 is opened and water or warm water is fed thereto. Next, the zipper 2 is closed and the bag is rubbed to mix the concentrated enteral nutrient in the liquid storage chamber 1 with water or warm water. And, the closing member 41 for the liquid exit 4 is twisted off and here e.g., a drip set of rubber tube type may be connected with the liquid exit. Incidentally, the prescribed amount of purified water or the like is stored in the bag, thereby it can also be mixed with a powder preparation for dialysis.

INDUSTRIAL APPLICABILITY

As be apparent from the above explanation, when using the liquid storage bag of the present invention, in case that liquid stored in the internal part is a concentrated enteral nutrient, it may be preserved for a long period of time without deterioration of its quality and a trouble of feeding water or the like therein can be saved. Since the bag has a virgin-proof faculty by an easily peelable partition wall (weak seal part), a check for the safety can also be conducted. Also, by making a shape of the weak seal part into such one that the center part thereof is an outside-convex form and that the width is gradually enlarged toward both end parts thereof, the openability of it by pressing the bag from the outside becomes easy and the opening of the weak seal part by impact from the dropping, etc. can be prevented.

The invention claimed is:

1. A liquid storage bag comprising:

a bag body having a top portion and a bottom portion, said bag body having an internal space therein;

an opening and closing device having ends in said top portion;

heat seals provided adjacent both ends of said opening and closing device;

a liquid outlet provided on said bottom portion;

a peelable partition wall having ends configured to divide in a liquid-tight manner said internal space into a lower space and an upper space; and including a hanging device adjacent one end of said opening and closing device, one end of said peelable partition wall, and one heat seal, wherein said partition wall has end portions and a central portion located at a center of said partition wall halfway between said end portions, said central portion having a convex shape, wherein said partition wall has a width that increases continuously from a reduced width portion at said center portion to increased width portions at said end portions where said width is defined as a distance between said upper space and said lower space, and said width of said end portions are at least two times greater than said width of said center portion.

2. The liquid storage bag as claimed in claim 1, wherein said partition wall is provided close to said opening and closing device.

3. The liquid storage bag as claimed in claim 1, wherein said opening and closing device is a zipper.

4. The liquid storage bag as claimed in claim 1, wherein a portion of said top portion of said bag body above said opening and closing device is provided with a sealed part to enclose said opening and closing device.

5. The liquid storage bag as claimed in claim 4, wherein a notch is formed in said bag body between said sealed part and said opening and closing device.

6. The liquid storage bag as claimed in claim 1, wherein said lower space has liquid stored therein.

7. The liquid storage bag as claimed in claim 6, wherein said liquid is a concentrated enteral nutrient.

8. The liquid storage bag as claimed in claim 1, wherein said increased width portions each have a width that is at least twice the width of said reduced width portion.

9. The liquid storage bag as claimed in claim 1, wherein said end portions of said partition wall connect to edges of said bag body.

* * * * *